United States Patent
Buathier et al.

(10) Patent No.: US 7,553,993 B2
(45) Date of Patent: Jun. 30, 2009

(54) PROCESS FOR THE PREPARATION OF 2,6-DIHALO-PARA-TRIFLUORO METHYLANILINE

(75) Inventors: Bernard Buathier, Saint-Cyr-Au-Mont-d'Or (FR); Pierre Le Roy, Lyons (FR)

(73) Assignees: BASF Agro B.V., Arnhem (NL); Wadenswil/AU (CH)

( * ) Notice: Subject to any disclaimer, the term of this patent is extended or adjusted under 35 U.S.C. 154(b) by 123 days.

(21) Appl. No.: 10/532,160

(22) PCT Filed: Oct. 24, 2003

(86) PCT No.: PCT/EP03/13340

§ 371 (c)(1), (2), (4) Date: Aug. 31, 2005

(87) PCT Pub. No.: WO2004/037766

PCT Pub. Date: May 6, 2004

(65) Prior Publication Data

US 2006/0142614 A1    Jun. 29, 2006

(30) Foreign Application Priority Data

Oct. 25, 2002    (FR) ................................. 02 13392

(51) Int. Cl.
*C07C 209/74*    (2006.01)
*C07C 211/00*    (2006.01)

(52) U.S. Cl. ........................ 564/412; 564/218; 564/442

(58) Field of Classification Search ................ 564/218, 564/412, 442

See application file for complete search history.

(56) References Cited

U.S. PATENT DOCUMENTS

| | | | |
|---|---|---|---|
| 4,384,135 A * | 5/1983 | Cartwright et al. | 562/435 |
| 6,479,703 B1 | 11/2002 | Ancel et al. | |
| 6,747,175 B2 * | 6/2004 | Kempf et al. | 564/412 |
| 2006/0142614 A1 | 6/2006 | Buathier et al. | |

FOREIGN PATENT DOCUMENTS

| | | |
|---|---|---|
| FR | 2 810 665 | 12/2001 |
| FR | 2 846 325 | 4/2004 |
| WO | WO-00/35851 | 6/2000 |
| WO | WO-01/64623 | 9/2001 |

OTHER PUBLICATIONS

Wikpedia, Protic Solvent, Wikipedia Foundation, Inc., Jul. 12, 2007, pp. 1.*
Tobe, Yoshito et al., "Novel Self-Assembly of m-Xylylene Type Dithioureas by Head-to-Tail Hydrogen Bonding", Journal of Organic Chemistry, 1998, pp. 7481-7489, vol. 63, American Chemical Society, Easton, US.

* cited by examiner

*Primary Examiner*—Porfirio Nazario-Gonzalez
*Assistant Examiner*—Yate' K Cutliff
(74) *Attorney, Agent, or Firm*—Brinks Hofer Gilson & Lione

(57) ABSTRACT

Process for the preparation of a compound of general formula (I):

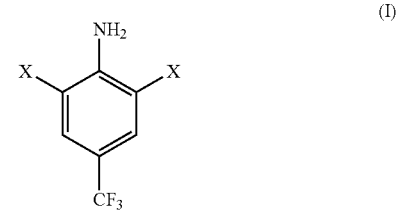

in which X represents a halogen atom,
by reaction of para-trifluoromethylaniline of formula (II):

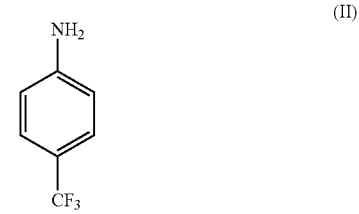

with a dihalogen $X_2$,
the two compounds being introduced simultaneously into a polar aprotic solvent in a dihalogen/compound (II) molar ratio ranging from 1.9 to 2.5 and at a temperature ranging from 100 to 300° C.

12 Claims, No Drawings

PROCESS FOR THE PREPARATION OF 2,6-DIHALO-PARA-TRIFLUORO METHYLANILINE

The present invention relates to a novel process for the preparation of a 2,6-dihalo-para-trifluoromethylaniline from para-trifluoromethylaniline.

Numerous studies have already been carried out with the aim of developing processes for the preparation of 2,6-dihalo-para-trifluoromethylanilines. Patent Application WO 00/35851 discloses a process for the preparation of a 2,6-dihalo-para-trifluoromethylaniline from a trihalo-para-trifluoromethylbenzene at a temperature of between 130 and 350° C. in a preferably polar solvent. The use of para-trifluoromethylaniline for the preparation of 2,6-dihalo-para-trifluoromethylaniline does not appear in this patent application.

Patent Applications FR 2 810 665 and WO 01/64623 disclose a process for the preparation of 2,6-dichloro-para-trifluoromethylaniline by chlorination of precursor anilines in a hydrofluoric acid medium. The precursor compound is trifluoromethylphenylcarbamoyl fluoride. The use of an other solvent than hydrofluoric acid is not mentioned.

Nevertheless, these processes result in the formation of impurities, such as polycondensates or heavy polychlorinated compounds, which make it impossible to use 2,6-dihalo-para-trifluoromethylaniline in the continuation of the preparation of pesticidal compounds of phenylpyrazole type without subjecting it to a prior purification stage. This purification stage constitutes a major disadvantage when it is a matter of preparing 2,6-dichloro-para-trifluoromethylaniline on an industrial scale, in particular for the production of pesticides of phenylpyrazole type.

It has now been discovered, in an entirely surprising way, that the process for the preparation of 2,6-dihalo-para-trifluoromethylaniline according to the present invention results in a compound which is sufficiently pure to be used directly in the continuation of the process for the production of pesticidal compounds of phenylpyrazole type.

A subject-matter of the present invention is thus a process for the preparation of a compound of general formula (I):

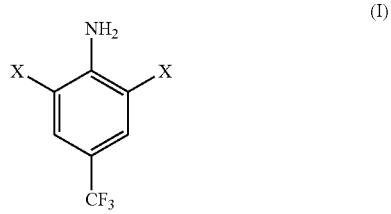

(I)

in which X represents a halogen atom, by reaction of para-trifluoromethylaniline of formula (II):

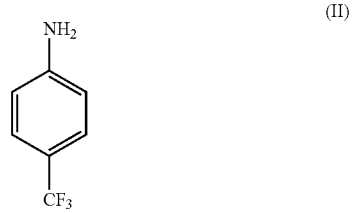

(II)

with a dihalogen $X_2$, the two compounds being introduced simultaneously into a polar aprotic solvent at a temperature ranging from 100 to 300° C. and at a dihalogen/compound (II) molar ratio ranging from 1.9 to 2.5.

In the context of the present invention, X represents a halogen atom. X can be a chlorine atom, a bromine atom, an iodine atom or a fluorine atom.

The compound of general formula (I) preferably prepared by virtue of the process according to the present invention is 2,6-dichloro-para-trifluoromethylaniline, which is particularly useful in the synthesis of fipronil, an insecticidal compound of phenylpyrazole type.

The solvent used during the preparation of the compound of general formula (I) according to the present invention is a polar aprotic solvent. A preferred polar aprotic solvent can be a chlorinated aromatic solvent, such as monochlorobenzene, or a chlorinated aliphatic solvent, such as dichloroethane. In an entirely preferred way, monochlorobenzene will be chosen as solvent.

The dihalogen/compound (II) molar ratio is chosen as ranging from 1.9 to 2.5 during the preparation of the 2,6-dihalo-para-trifluoromethylaniline according to the present invention. The dihalogen/compound (II) molar ratio is preferably chosen as ranging from 2 to 2.05.

The temperature of the reaction medium according to the present invention is chosen as ranging from 100 to 300° C. The temperature of the reaction medium is preferably chosen as ranging from 100 to 130° C. In an entirely preferred way, the temperature of the reaction medium is chosen as ranging from 105° C. to 115° C.

In an entirely preferred way, the process according to the present invention consists in preparing 2,6-dichloro-para-trifluoromethylaniline by simultaneously introducing para-trifluoromethylaniline and $Cl_2$ into monochlorobenzene in a $Cl_2$/para-trifluoromethylaniline molar ratio of between 1.85 and 2.05, at a temperature ranging from 105 to 115° C.

The process according to the present invention can be carried out according to general techniques known to a person skilled in the art. Thus, the process according to the present invention can be carried out in a jacketed reactor equipped with a stirring device and surmounted by a reflux condenser maintained at a temperature of less than or equal to −10° C. The halogen necessary for the reaction will be introduced via a dip pipe arriving with stirring. The stirrer preferably used will make it possible to provide optimum micromixing of the reactants. This can be carried out by a stirrer of impeller type or by any other stirrer well known to a person skilled in the art.

During the reaction according to the present invention, hydrochloric acid in the gaseous form is produced. The latter is subsequently generally absorbed by a sodium hydroxide trap. As para-trifluoromethylaniline reacts instantaneously on contact with hydrochloric acid to form para-trifluoromethylaniline hydrochloride, para-trifluoromethylaniline will preferably be fed to the reactor via a dip pipe, in order to avoid blockages.

During the introduction of the reactants, a marked tendency to foam is sometimes observed. This can generally be avoided by reducing the flow rate for the introduction of the reactants. Nevertheless, in order to avoid the accumulation of foam, the latter should be taken up by the liquid. One answer is therefore generally to increase the stirring rate.

The product obtained by virtue of the process according to the present invention (2,6-dihalo-para-trifluoromethylaniline) has a sufficient degree of purity to be reused directly in the synthesis of the pesticidal compounds of phenylpyrazole type. It is generally considered that the degree of purity should be at least 96% in order for the product to be able to be used in the continuation of a preparation process.

The 2,6-dihalo-para-trifluoromethylaniline obtained can also be isolated, in particular in order to be stored, by distillation of the solvent according to techniques known to a person skilled in the art.

The example of the preparation of compounds which follows is mentioned with the aim of illustrating the invention but should on no account be regarded as limiting the latter.

Preparation of 98% 2,6-dichloro-para-trifluoromethylaniline 12 140 kg of pure monochlorobenzene are charged to a 20 m³ jacketed reactor rendered inert with nitrogen. The solvent heel is subsequently brought to 110° C. by heating the jacket.

The reactor is subsequently fed with a 70% solution of para-trifluoromethylaniline in monochlorobenzene at a flow rate of 792 kg/h for 6 h 30 and with $Cl_2$ at a flow rate of 488 kg/h. The temperature is maintained at 110° C. by cooling the jacket.

Once feeding is complete, the residual content of para-trifluoromethylaniline or of monochloro derivative is monitored. If one of these compounds remains, it is then advisable to adjust the amount of chlorine in order to consume the residual product.

At the end of the reaction, the monochlorobenzene is distilled off by placing the reactor under gradually increasing vacuum through a distillation column. After removal of the solvent, the 2,6-dichloro-para-trifluoromethylaniline is cooled to 60° C. before emptying the reactor to the storage tank.

The product obtained according to the process described above was analysed. The results given in the table below correspond to the mean of the analytical results which are obtained for the product over a period of one year:

| DCpTFMA assay (solvent-free) | p-TFMA assay (solvent-free) | Monochloro-para-trifluoromethylaniline assay |
|---|---|---|
| 98.1% | 0.05% | 0.09% |

These results thus show that the 2,6-dichloro-para-trifluoromethylaniline obtained by the process according to the present invention is pure to greater than 98%, that the reaction yield is very good, since only 0.05% of reactant (p-TFMA) remains, and that only 0.09% of the monochloro-para-trifluoromethylaniline has not been converted to 2,6-dichloro-para-trifluoromethylaniline.

What is claimed is:

1. Process for the preparation of a compound of general formula (I):

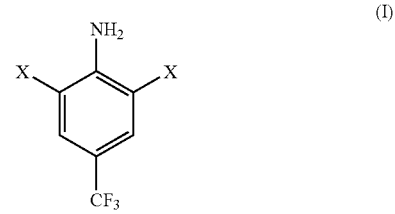

in which X represents a halogen atom, by reaction of para-trifluoromethylaniline of formula (II):

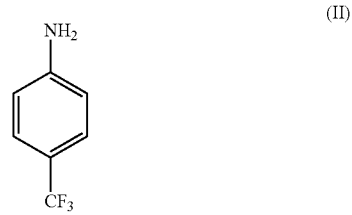

with a dihalogen $X_2$, the two compounds being introduced simultaneously into a polar aprotic solvent in a dihalogen/compound (II) molar ratio ranging from 1.9 to 2.5 and at a temperature ranging from 100 to 300° C., without the addition of hydrofluoric acid.

2. Process according to claim 1, characterised in that the compound of formula (I) is 2,6-dichloro-para-trifluoromethylaniline.

3. Process according to claim 1, wherein the solvent used is a chlorinated aliphatic solvent.

4. Process according to claim 3, characterised in that the solvent used is dichloroethane.

5. Process according to claim 1, wherein the solvent used is a chlorinated aromatic solvent.

6. Process according to claim 5, characterised in that the solvent used is monochlorobenzene.

7. Process according to claim 1, wherein, the reactants are introduced in a dihalogen/compound (II) molar ratio ranging from 2 to 2.05.

8. Process according to claim 1, wherein the temperature of the reaction medium is chosen as ranging from 100 to 130° C.

9. Process according to claim 8, characterised in that the temperature of the reaction medium is chosen as ranging from 105 to 115° C.

10. Process according to claim 2, characterized in that the reactants are introduced into monochlorobenzene in a dichlorine/compound (II) molar ratio ranging from 1.85 to 2.05, at a temperature ranging from 105 to 115° C.

11. Process according to claim 2, wherein the solvent used is a chlorinated aliphatic solvent.

12. Process according to claim 2, wherein the solvent used is a chlorinated aromatic solvent.

* * * * *